United States Patent
Hu et al.

(10) Patent No.: US 7,649,173 B2
(45) Date of Patent: Jan. 19, 2010

(54) METHOD OF PREPARING A SAMPLE FOR TRANSMISSION ELECTRON MICROSCOPY

(75) Inventors: Jianqiang Hu, Shanghai (CN); Zhixian Rui, Shanghai (CN); Yanli Zhao, Shanghai (CN); Yanjun Wang, Shanghai (CN); Ming Li, Shanghai (CN); Min Pan, Shanghai (CN)

(73) Assignee: Semiconductor Manufacturing International (Shanghai) Corporation, Shanghai (CN)

( * ) Notice: Subject to any disclaimer, the term of this patent is extended or adjusted under 35 U.S.C. 154(b) by 579 days.

(21) Appl. No.: 11/618,728

(22) Filed: Dec. 29, 2006

(65) Prior Publication Data

US 2008/0078742 A1    Apr. 3, 2008

(30) Foreign Application Priority Data

Sep. 30, 2006    (CN)    .................... 2006 1 0116910

(51) Int. Cl.
G01N 23/00    (2006.01)
G21K 7/00    (2006.01)

(52) U.S. Cl. .................... 250/307; 257/10; 257/11; 257/48; 438/745; 216/33; 216/39; 216/57

(58) Field of Classification Search ............ None
See application file for complete search history.

(56) References Cited

U.S. PATENT DOCUMENTS

| | | | |
|---|---|---|---|
| 6,042,736 A * | 3/2000 | Chung | 216/33 |
| 7,112,790 B1 * | 9/2006 | Wang | 250/307 |
| 7,138,628 B2 * | 11/2006 | Tomimatsu et al. | 250/306 |
| 7,297,965 B2 * | 11/2007 | Kidron et al. | 250/492.2 |

* cited by examiner

*Primary Examiner*—Duy-Vu N Deo
(74) *Attorney, Agent, or Firm*—Squire, Sanders & Dempsey, L.L.P.

(57) ABSTRACT

A method for preparing TEM sample, comprising the following steps: providing a sample with two pits and a failure region between the two pits, the failure region comprising a semiconductor device; milling the first surface of the failure region, till the cross section of the semiconductor device is exposed; etching the first surface of the failure region; cleaning the sample; milling the second surface of the failure region, till the failure region can be passed by electron beam. A sample can be prepared for a high resolution TEM through above steps. When the sample is observed, it is easy to distinguish the lightly doped drain, source/drain regions from the silicon substrate and observe the pattern and defects in the lightly doped drain, source/drain regions clearly; in addition, it is easy to distinguish the BPSG from the non-doped silicon dioxide in the failure region.

15 Claims, 6 Drawing Sheets

METHOD OF PREPARING A SAMPLE FOR TRANSMISSION ELECTRON MICROSCOPY

This application claims the priority of Chinese Patent Application 200610116910.1, filed Sep. 30, 2006, the entire disclosure of which is incorporated herein by reference.

FIELD OF THE INVENTION

The invention relates to a method of preparing a sample for transmission electron microscopy (TEM).

BACKGROUND OF THE INVENTION

With the development of Very Large Scale Integration (VLSI), lightly doped drain (LDD) and source/drain regions are employed in deep submicron systems. In order to make the source/drain expansion region shallower so as to control the short channel effect, a large amount of impurities are often used as dopant in an area near the channel of the source/drain PN junction to control the depth of the LDD region and the source/drain expansion region. However, implanting a large amount of impurities into the small region by the ion implantation method will cause defects, resulting in a leakage current in the PN junction and then damaging the semiconductor device.

In general, a secondary ion mass spectrometer (SIMS) method is used to perform a failure analysis for semiconductor devices. However, the SIMS method usually is time-consuming due to its low detection speed and therefore is not suitable for analyzing a small region. In addition, the SIMS method can only be used to detect defects in wafers other than semiconductor devices. Thus the detection result cannot faithfully represent defects in the final products.

Due to its high resolution, the TEM can be used to observe the patterns and dimensions of very thin films. Therefore, as the dimensions of semiconductor devices become smaller and smaller, especially when the device width is less than 0.13 µm, the TEM has become an important apparatus for observing and analyzing defects and structures in integrated circuits. FIG. 1A-1C are schematic diagrams of TEM samples fabricated by existing methods. As shown in FIG. 1A, a failure region 103 is positioned on the sample 100 by a method of electrical positioning. Two pits 101 and 102 having a larger area than the failure region 103 are dug out at both sides of the failure region 103 in the sample 100 using a focused ion beam (FIB) with a current of 7000 pA. As a result, the cross section of the failure region 103 can be observed during the subsequent process of milling the failure region 103, and the failure region 103 can be taken out from the sample 100 easily. The pits 101 and 102 are 15 µm×8 µm×6 µm (length×width×depth) (the dimension along the X-axis is defined as the length; the dimension along the Y-axis is defined as the width; and the dimension along the Z-axis is defined as the depth; the same below). The failure region 103 between the pits 101 and 102 is 3 µm-12 µm in length and 1 µm-3 µm in width. As shown in FIG. 1B, the current for FIB is adjusted to 300 pA and is used to mill the first surface 104 of the failure region 103, until the cross section of the failure region 103 for the semiconductor device is exposed. The milling depth is 4 µm. The second surface 105 of the observation region 103 is milled by FIB with a current of 300 pA, until the width of the failure region 103 is 80 nm-120 nm. As shown in FIG. 1C, the sample 100 is placed into a TEM observation chamber, and the failure region 103 is irradiated with an electron beam accelerated by a high voltage. The pattern of the failure region 103 for a semiconductor device is magnified and projected onto a screen for analysis.

The existing method for preparing TEM samples is disclosed by JP2004245841.

FIGS. 2A-2B are schematic diagrams of TEM samples prepared by existing methods. As shown in FIG. 2A, a cross section of the failure region for a semiconductor device is observed by a TEM with an amplifying multiple of 97000. The lightly doped drain 110 and source 112 are ion doped regions, and the silicon substrate 114 is a non-doped region. Since the ion doped regions are in the same thickness as the non-doped region, it is difficult to distinguish the lightly doped drain 110 and source 112 regions from the silicon substrate 114 and to clearly observe the pattern and defects in the lightly doped drain 110 and source 112 regions.

As shown in FIG. 2B, the pattern in the lightly doped drain and the source regions is observed by TEM with an amplifying multiple of 97000. The lightly doped drain 116 and drain 118 regions are ion doped regions, and the silicon substrate 120 is a non-doped region. Since the ion doped region are in the same thickness as the non-doped region, it is difficult to distinguish the lightly doped drain 116 and drain 118 regions from the silicon substrate 120 and to clearly observe the pattern and defects in the lightly doped drain 116 and source 118 regions.

Since the lightly doped drain, source/drain regions in the TEM sample prepared by FIB according to existing methods are in the same thickness as the silicon substrate, it is difficult to distinguish the lightly doped drain, source/drain regions from the silicon substrate and to clearly observe the pattern and defects in the lightly doped drain, source/drain regions.

SUMMARY OF THE INVENTION

An object of the present invention is to provides a method for preparing a TEM sample so as to avoid the problem that it is difficult to distinguish the lightly doped drain, source/drain regions from the silicon substrate and to clearly observe the pattern and defects in the lightly doped drain, source/drain regions, since the lightly doped drain, source/drain regions are in the same thickness as the silicon substrate.

To solve above this and other problems, a TEM sample preparation method is provided, which comprises the following steps: providing a sample with two pits and a failure region between the two pits, the failure region comprising a semiconductor device; milling the first surface of the failure region until the cross section of the semiconductor device is exposed; etching the first surface of the failure region; cleaning the sample; milling the second surface of the failure region until the failure region can be passed by an electron beam.

The first surface of the failure region is etched with a mixed acid solution comprising nitrate acid, hydrofluoric acid, acetic acid, and copper sulfate, wherein the mass percentage of nitrate acid is 45%-60%, the mass percentage of hydrofluoric acid is 4.5%-5%, the nitrate acid is 10 ml-15 ml, the hydrofluoric acid is 5 ml-10 ml, the acetic acid is 80 ml-100 ml, and the copper sulfate is 0.2 g-0.5 g. The time for etching the first surface of the failure region is 7 s-9 s.

Next, the first and second surfaces of the failure region are milled by FIB with a current of 300 pA-500 pA.

The sample is cleaned by distilled water or deionized water for 60 s-120 s.

The second surface of the failure region is milled until the thickness of the failure region which can be passed by the electron beam is 80 nm-120 nm.

Because an etching process by acid is added during preparing the TEM sample by FIB, the invention has following advantages over the existing method. Since the lightly doped drain, source/drain regions are ion doped regions, the acid solution will react with the ions in the lightly doped drain, source/drain regions. Since the silicon substrate is a non-doped region, the acid solution will not react with the silicon substrate. Therefore, the etching speed of the ion doped regions by the acid solution is faster than that of the non-doped region. As a result, the lightly doped drain, source/drain regions will be thinner than the silicon substrate after the etching process with acid. When this sample is observed in TEM, it is easy to distinguish the lightly doped drain, source/drain regions from the silicon substrate and to clearly observe the pattern and defects in the lightly doped drain, source/drain regions. Moreover, it is easy to distinguish the boro-phospho-silicate-glass (BPSG) from the non-doped silicon dioxide in the failure regions.

DETAILED DESCRIPTION OF THE INVENTION

There are various test apparatus in the semiconductor manufacturing industry, among which the TEM is an important tool to observe film patterns, dimensions, and properties of devices. The basic principles of TEM are as follows: thinning the sample to be observed by cutting, milling, and ion thinning; placing the sample into the TEM observation chamber; irradiating the sample with the electron beam accelerated by a high voltage; magnifying the pattern of the sample; and projecting it onto a screen; and then analyzing the sample. Due to the fact that the lightly doped drain, source/drain regions in the TEM sample prepared by FIB according to existing methods are in the same thickness as the silicon substrate, it is difficult to distinguish the lightly doped drain, source/drain regions from the silicon substrate and to clearly observe the pattern and defects in the lightly doped drain, source/drain regions. An etching process by acid is added during the preparation of the TEM sample according to the present invention. Since the lightly doped drain, source/drain regions are ion doped regions, the acid solution will react with the ions in the lightly doped drain, source/drain regions. Since the silicon substrate is a non-doped region, the acid solution will not react with the silicon substrate. Therefore, the etching speed of the ion doped regions by the acid solution is faster than that of the non-doped region. As a result, the lightly doped drain, source/drain regions will be thinner than the silicon substrate after the etching process by acid. When this sample is observed in TEM, it is easy to distinguish the lightly doped drain, source/drain regions from the silicon substrate and to clearly observe the pattern and defects in the lightly doped drain, source/drain regions. In addition, it is easy to distinguish the BPSG from the non-doped silicon dioxide in the failure regions. A more complete appreciation of the invention, and many of the attendant advantages thereof, will be readily apparent as the same becomes better understood by reference to the following detailed description when considered in conjunction with the accompanying drawings.

Figure 1A:
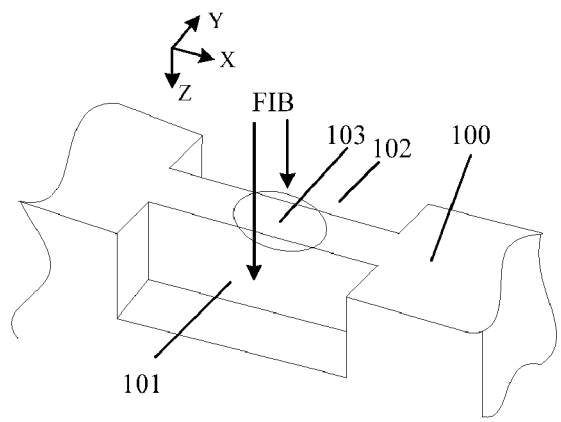
FIG. 1A-1C are schematic diagrams of the procedure for preparing TEM samples by existing methods.
Figure 1B:
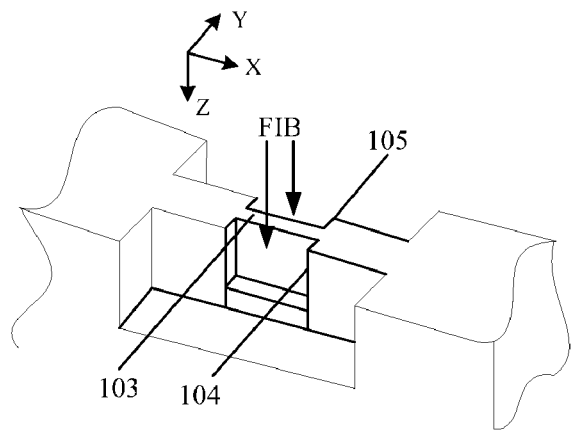
Figure 1C:
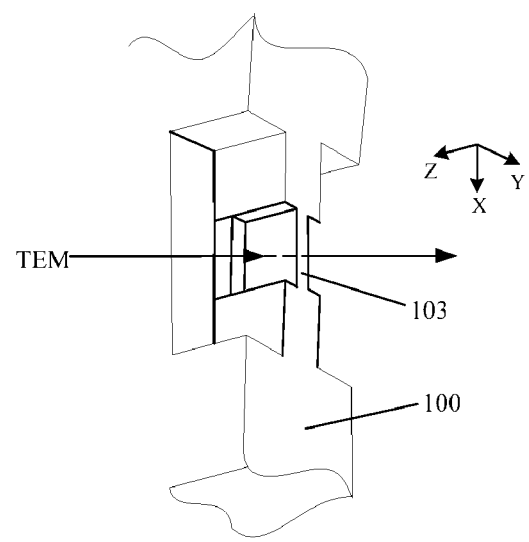
Figure 2A:
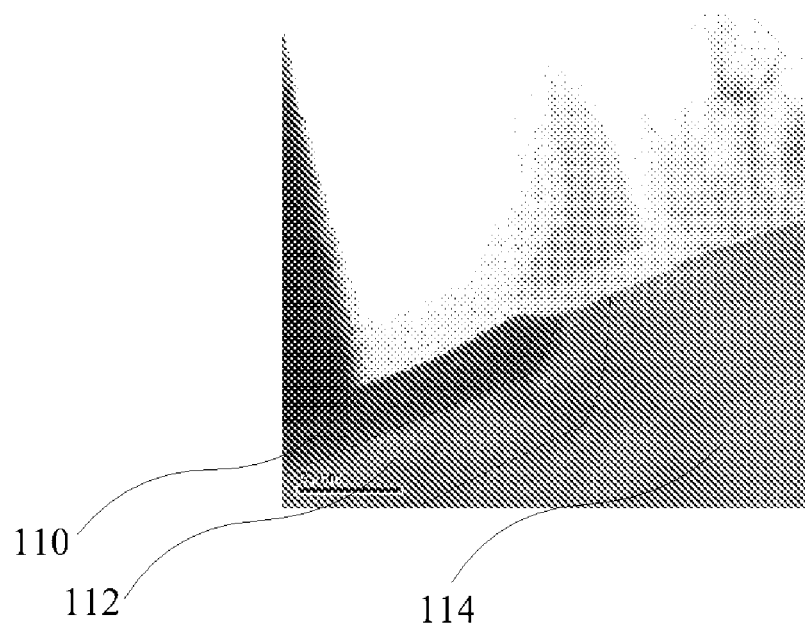
FIG. 2A-2B are schematic diagrams of TEM samples prepared by existing methods.
Figure 2B:
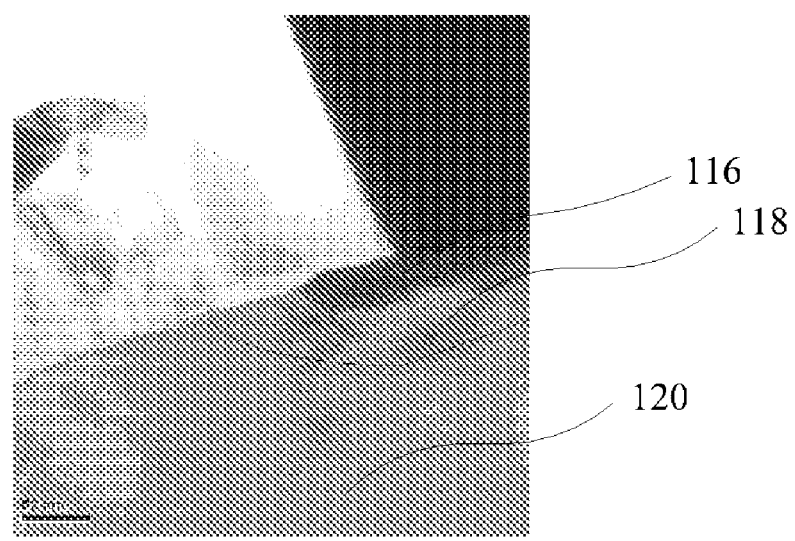
Figure 3:
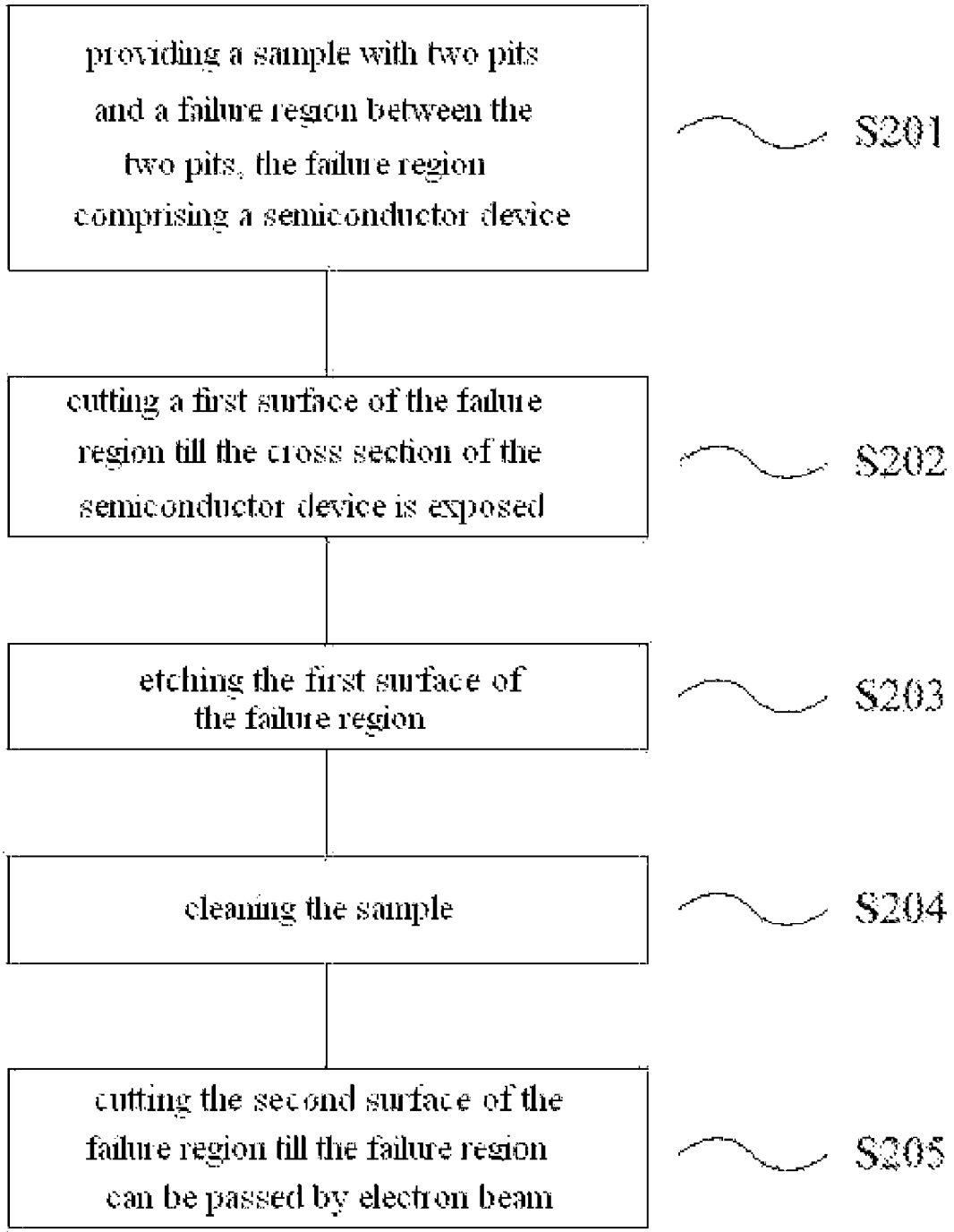
FIG. 3 is a flow chart of the method for preparing TEM samples according to the present invention.

FIG. 3 is a flow chart of the method for preparing TEM samples according to the present invention. At S201, a sample with two pits and a failure region between two pits is provided, the failure region comprising a semiconductor device. At S202, the first surface of the failure region is milled until the cross section of the semiconductor device is exposed. At S203, the first surface of the failure region is etched. At S204, the sample is cleaned. At S205, the second surface of the failure region is milled until the failure region can be passed by the electron beam.

Figure 4A:
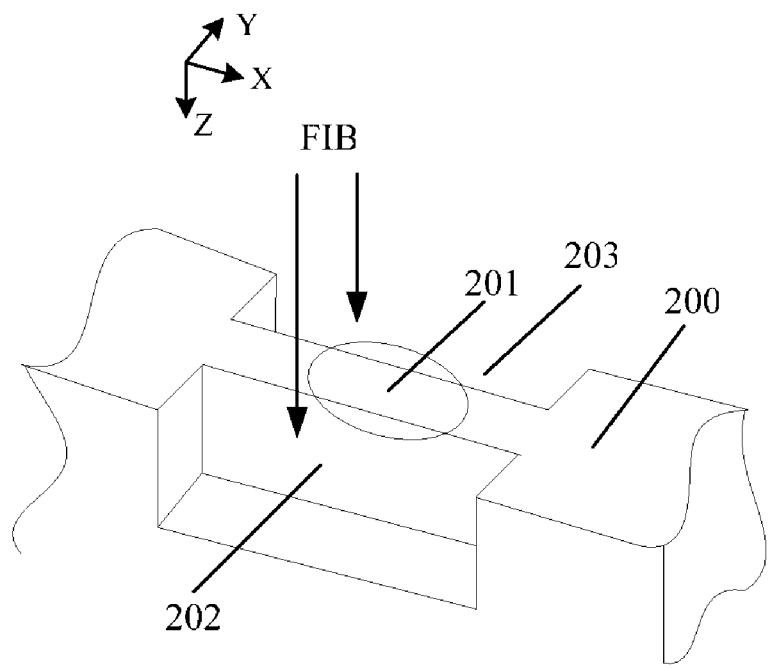
FIG. 4A-4D are schematic diagrams of the procedure for preparing TEM samples according to the present invention.

FIGS. 4A-4D are schematic diagrams of the procedure for preparing TEM samples according to the present invention. In the first embodiment of the invention, as shown in FIG. 4A, the failure region 201 is first positioned on the sample 200 using an electrical positioning method, i.e., using an emission microscope (EMMI) or an optical beam induced resistance change (OBIRCH) tool. The sample 200 is placed into the FIB apparatus, and positions and dimensions of the pits are defined by a software in the FIB apparatus. The surface of sample 200 is bombarded by FIB with a current of 500 pA-7000 pA to form the pits 202 and 203 having a larger area than the failure region 201 at both sides of the failure region 201, so that the cross section of the failure region 201 can be observed during the subsequent process for milling the failure region 201, and the failure region 201 can be taken out from the sample 200 easily. The pits 202 and 203 are 10 µm-20 µm in length, 5 µm-10 µm in width, and 2 µm-5 µm in depth. The failure region 201 is 3 µm-12 µm in length and 1 µm-3 µm in width. The dimension along the X-axis is defined as the length, the dimension along the Y-axis is defined as the width, and the dimension along the Z-axis is defined as the depth (the same below).

Figure 4B:
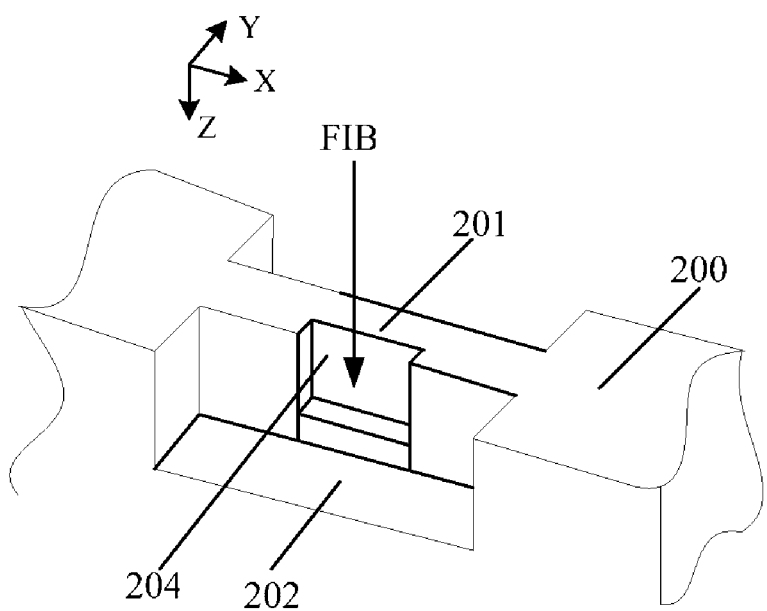

As shown in FIG. 4B, the current for FIB is regulated to 300 pA-500 pA and is used to mill the first surface 204 of the failure region 201 until the cross section of the failure region for the semiconductor device is exposed. In this embodiment, the first surface 204 is milled until the lightly doped drain and source/drain regions are exposed, and the first surface 204 of the failure region 201 is near the pit 202, wherein the first surface 204 is milled to 1 µm-4 µm in depth. Next, the sample 200 is taken out from the FIB apparatus, and the first surface 204 of the failure region 201 which has been milled is etched using a mixed acid solution. Then, the sample 200 is cleaned by distilled water or deionized water. Subsequently, the sample 200 is dried by blowing nitrogen on it.

Figure 4C:
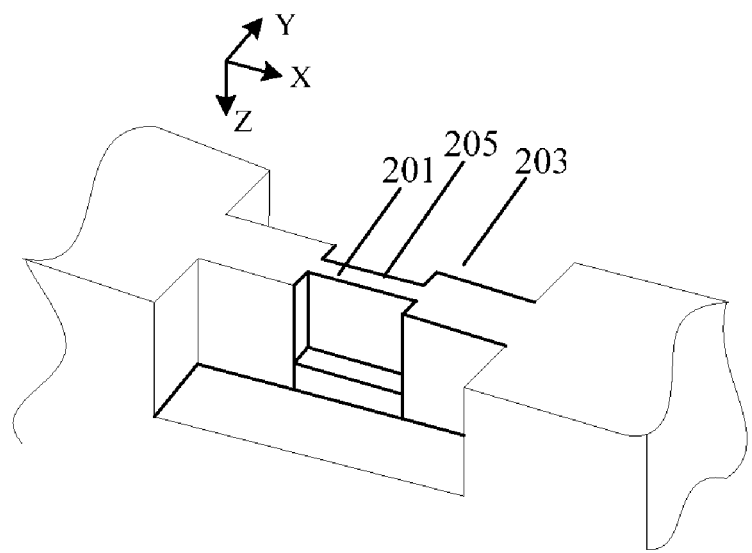

As shown in FIG. 4C, the sample 200 is placed into the FIB apparatus again. Next, the second surface 205 of the failure region 201 is milled by FIB with a current of 300 pA-500 pA until the failure region 201 can be passed by electron beam, and the thickness is from 80 nm to 120 nm. The second surface 205 of the failure region 201 is near the pit 203, wherein the second surface 205 is milled to a depth of 1 µm-4 µm.

Figure 4D:
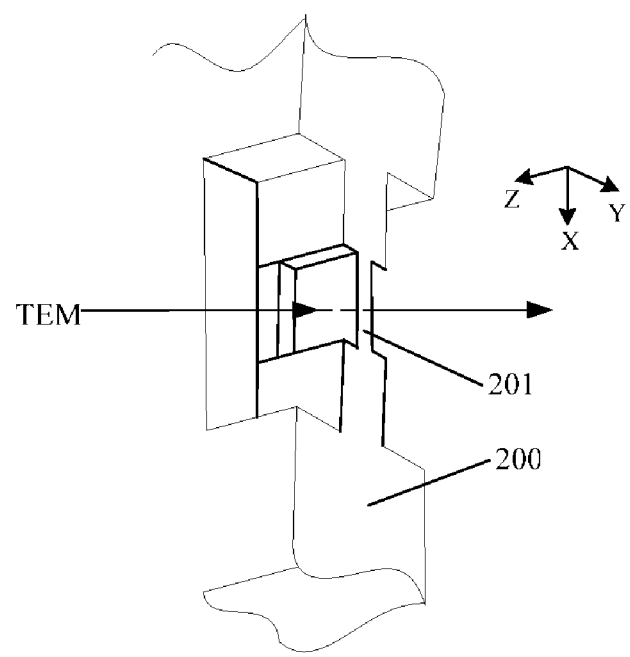

As shown in FIG. 4D, the sample is then placed into the TEM observation chamber, and the failure region 201 is irradiated by electron beam at a high voltage of 100 KV-500 KV; next, the pattern of failure region 201 in the lightly doped drain and source/drain regions of the semiconductor device is magnified and projected onto the screen for analysis.

In this embodiment, the mixed acid solution consists of nitrate acid, hydrofluoric acid, acetic acid and copper sulfate. Wherein, the mass percentage of nitrate acid is 45%-60%, specifically 45%, 50%, 55%, or 60%, preferably 45% in this embodiment. The mass percentage of hydrofluoric acid is 4.5%-5%, specifically 4.5%, 4.6%, 4.7%, 4.8%, 4.9% or 5%, preferably 4.9% in this embodiment. The nitrate acid is 10 ml-15 ml, specifically 10 ml, 11 ml, 12 ml, 13 ml, 14 ml or 15 ml; the hydrofluoric acid is 5 ml-10 ml, specifically 5 ml, 6 ml, 7 ml, 8 ml, 9 ml or 10 ml. The acetic acid is 80 ml-100 ml, specifically 80 ml, 85 ml, 90 ml, 95 ml or 100 ml. The copper sulfate is 0.2 g-0.5 g, specifically 0.2 g, 0.3 g, 0.4 g or 0.5 g. The time for etching the sample by the mixed acid solution is 7 s-9 s, specifically 7 s, 8 s, or 9 s.

In this embodiment, the surface of the sample 200 is bombarded by FIB with a current of 500 pA-700 pA to form pits 202 and 203 having a larger area than the failure region 201 at both sides of the failure region 201. Specifically, the current for FIB is 500 pA, 5500 pA, 6000 pA, 6500 pA or 7000 pA, preferably 7000 pA in this embodiment. The pits 202 and 203 are 15 μm in length, 8 μm in width and 3 μm in depth; in addition to this embodiment, the pits 202 and 203 can be 10 μm-20 μm in length, specifically 10 μm, 12 μm, 15 μm, 18 μm or 20 μm, preferably 15 μm in this embodiment. The pits 202 and 203 can be 5 μm-10 μm in width, specifically 5 μm, 7 μm, 8 μm or 10 μm, preferably 8 μm in this embodiment. The pits 202 and 203 can be 2 μm-5 μm in depth, specifically 2 μm, 3 μm, 4 μm or 5 μm, preferably 6 μm in this embodiment. The failure region 201 is 3 μm-12 μm in length, specifically 3 μm, 5 μm, 7 μm, 9 μm, 10 μm or 12 μm; and 1 μm-3 μm in width, specifically 1 μm, 2 μm or 3 μm, preferably 1 μm in this embodiment.

In this embodiment, the first surface 204 and the second surface 205 of the failure region 201 are bombarded by FIB with a current of 300 pA-500 pA, specifically 300 pA, 350 pA, 400 pA, 450 pA or 500 pA, preferably 300 pA in this embodiment.

The first surface 204 and the second surface 205 are milled to a depth of 1 μm-4 μm, specifically 1 μm, 2 μm, 3 μm or 4 μm, preferably 4 μm in this embodiment.

The sample 200 is cleaned with distilled water or deionized water for 60 s-120 s, specifically 60 s, 70 s, 80 s, 90 s, 100 s, 110 s or 120 s, preferably 60 s in this embodiment.

The sample is dried by blowing nitrogen in this embodiment, or, it can be dried naturally also.

In this embodiment, the first surface 204 of the failure region 201 is milled till the cross section of the failure region for the semiconductor device is exposed. The first surface 204 of the failure region 201 is etched. Then the sample 200 is cleaned and dried by blowing. Next, the second surface 205 of the failure region 201 is milled, till the thickness of the failure region 201 which can be passed by the electron beam is 80 nm-120 nm, specifically 80 nm, 90 nm, 100 nm, 110 nm or 120 nm. In addition to this embodiment, the second surface 205 of the failure region 201 can be milled at first, till the cross section of the failure region for the semiconductor device is exposed; then, the second surface 205 of the failure region 201 is etched, and the sample 200 is cleaned and dried by blowing; next, the first surface 204 of the failure region 201 is milled, till the thickness of the failure region 201 which can be passed by the electron beam is 80 nm-120 nm.

Next, the second embodiment of the method for preparing TEM samples according to the invention is described referring to FIG. 4A to 4D. As shown in FIG. 4A, firstly, the failure region 201 is positioned on the sample 200 by an electrical positioning method, i.e., by means of EMMI or OBIRCH tool; next, the sample 200 is placed into the FIB apparatus, and the positions and dimensions of the pits are defined by a software in the FIB apparatus; next, the surface of the sample 200 is bombarded by FIB with a current of 5000 pA-7000 pA to form pits 202 and 203 having a larger area than the failure region 201 at both sides of the failure region 201, so that the cross section of the failure region 201 can be observed during the subsequent process for milling the failure region 201 and the failure region 201 can be taken out from the sample 200 easily; the pits 202 and 203 are 15 μm in length, 8 μm in width, and 6 μm in depth; the failure region 201 is 1μm.

As shown in FIG. 4B, the current for FIB is regulated to 300 pA-500 pA and is used to mill the first surface 204 of the failure region 201, till the cross section of the failure region for the semiconductor device is exposed. In this embodiment, the first surface 204 is milled till the lightly doped drain and source/drain regions are exposed, and the first surface 204 of the failure region 201 is near the pit 202; wherein, the first surface 204 is milled to a depth of 4 μm; next, the sample 200 is taken out from the FIB apparatus, and the sample which has been milled is etched by a mixed acid solution including nitrate acid, hydrofluoric acid and acetic acid for 7 s; wherein, the nitrate acid is 20 ml and has a mass percentage of 65%; the hydrofluoric acid is 1 ml and has a mass percentage of 49%; and the acetic acid is 100 ml; next, the sample 200 is cleaned with distilled water or deionized water for 60 s-120 s; then, the sample 200 is dried by blowing nitrogen.

As shown in FIG. 4C, the sample 200 is placed into the FIB apparatus again; next, the second surface 205 of the failure region 201 is milled by FIB with a current of 300 pA-500 pA, till the thickness of the failure region 201 which can be passed by the electron beam is 80 nm-120 nm; the second surface 205 of the failure region 201 is near the pit 203; wherein, the second surface 205 is milled to 4 μm in depth.

As shown in FIG. 4D, the sample is then placed into the TEM observation chamber, and the failure region 201 is irradiated by the electron beam at a high voltage of 100 KV-500 KV. Next, the pattern of failure region 201 in the lightly doped drain and source/drain regions for the semiconductor device is magnified and projected onto the screen for analysis.

In this embodiment, the surface of the sample 200 is bombarded by FIB with a current of 5000 pA-7000 pA to form pits 202 and 203 having a larger area than the failure region 201 at both sides of the failure region 201; specifically, the current for FIB is 5000 pA, 5500 pA, 6000 pA, 6500 pA or 7000 pA, preferably 7000 pA in this embodiment. The pits 202 and 203 are 15 μm in length, 8 μm in width and 6 μm in depth. In addition to this embodiment, the pits 202 and 203 can be 10 μm-20 μm in length, specifically 10 μm, 12 μm, 15 μm, 18 μm or 20 μm; the pits 202 and 203 can be 5 μm-10 μm in width, specifically 5 μm, 7 μm, 8 μm or 10 μm; and the pits 202 and 203 can be 2 μm-5 μm in depth, specifically 2 μm, 3 μm, 4 μm or 5 μm.

In this embodiment, the first surface 204 and the second surface 205 of the failure region 201 are milled by FIB with a current of 300 pA-500 pA, specifically 300 pA, 350 pA, 400 pA, 450 pA or 500 pA, preferably 300 pA in this embodiment.

The sample 200 is cleaned with distilled water or deionized water for 60 s-120 s, specifically 60 s, 70 s, 80 s, 90 s, 100 s, 110 a or 120 s, preferably 60 s in this embodiment.

The sample is dried by blowing nitrogen onto it in this embodiment, or, it can also be dried naturally.

In this embodiment, the first surface 204 of the failure region 201 is milled until the cross section of the failure region for the semiconductor device is exposed. Then, the first surface 204 of the failure region 201 is etched, and then the sample 200 is cleaned and dried by blowing. Next, the second surface 205 of the failure region 201 is milled until the thickness of the failure region 201 which can be passed by the electron beam is 80 nm-120 nm, specifically 80 nm, 90 nm, 100 nm, 110 nm or 120 nm. In addition to this embodiment, the second surface 205 of the failure region 201 can be milled firstly until the cross section of the failure region for the semiconductor device is exposed. Then, the second surface 205 of the failure region 201 is etched, and the sample 200 is cleaned and dried by blowing. Next, the first surface 204 of the failure region 201 is milled until the thickness of the failure region 201 which can be passed by the electron beam is 80 nm-120 nm.

Figure 5A:
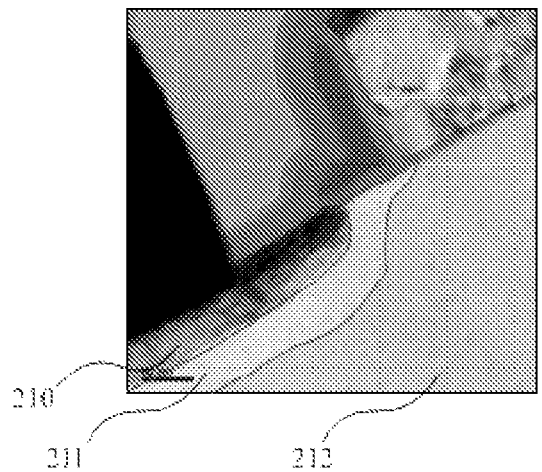
FIG. 5A-5C are schematic diagrams of TEM samples prepared according to the present invention.
Figure 5B:
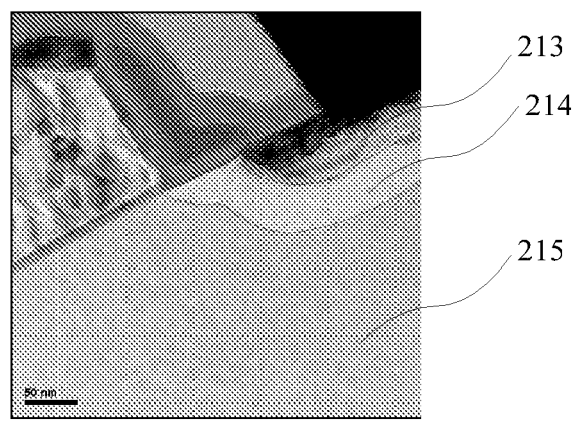
Figure 5C:
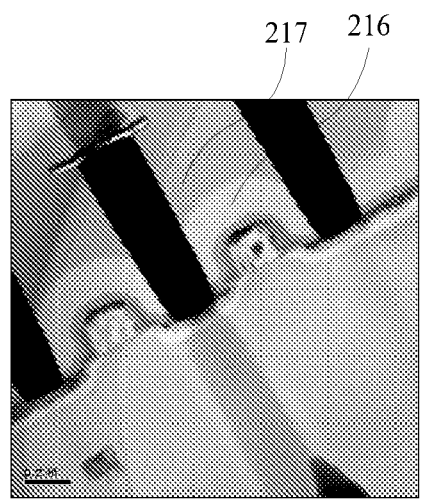

FIGS. 5A-5C are schematic diagrams of TEM samples prepared according to the invention. As shown in FIG. 5A, the TEM samples shown in FIGS. 4A-4D are observed by TEM with an amplifying multiple of 97000. Since the lightly doped drain 210 and source 211 regions are ion doped regions, the acid solution will react with the ions in the lightly doped drain 210 and source 211 regions. Since the silicon substrate 212 is a non-doped region, the acid solution will not react with the silicon substrate 212. Therefore, the etching speed of the lightly doped drain 210 and source 211 regions by the acid solution is higher than that of the silicon substrate 212 region. As a result, the lightly doped drain 210 and source 211 regions are thinner than the silicon substrate 212 region after the etching process, and it is easy to distinguish the lightly doped drain 210 and source 211 regions from the silicon substrate 212 region and to clearly observe the pattern and defects in the lightly doped drain 210 and source 211 regions.

As shown in FIG. 5B, the TEM samples shown in FIGS. 4A-4D are observed by TEM with an amplifying multiple of 97000. Since the lightly doped drain 213 and drain 214 regions are ion doped regions, the acid solution will react with the ions in the lightly doped drain 213 and drain 214 regions. Since the silicon substrate 215 is a non-doped region, the acid solution will not react with the silicon substrate 215. Therefore, the etching speed of the lightly doped drain 213 and drain 214 regions by the acid solution is higher than that of the silicon substrate 215 region. As a result, the lightly doped drain 213 and drain 214 regions are thinner than the silicon substrate 215 region after the etching process, and thus it is easy to distinguish the lightly doped drain 213 and drain 214 regions from the silicon substrate 215 region and to clearly observe the pattern and defects in the lightly doped drain 213 and drain 214 regions.

As shown in FIG. 5C, the TEM samples shown in FIG. 4A-4D are observed by TEM with an amplifying multiple of 97000. Since the BPSG region is an ion doped region, the acid solution will react with boron and phosphor in the BPSG region. Since the non-doped silicon dioxide 217 is a non-doped region, the acid solution will not react with the non-doped silicon dioxide 217. Therefore, the etching speed of BPSG region by the acid solution is higher than that of the non-doped silicon dioxide 217 region. As a result, the BPSG 216 region is thinner than the non-doped silicon dioxide 217 region after the etching process, and thus it is easy to distinguish the BPSG 216 region from the non-doped silicon dioxide 217 region.

While the preferred embodiments of the present invention have been described as above, the scope of the present invention shall not be limited thereto, and those skilled in the art can make various variations and modifications to the embodiments without departing from the scope of the present invention. All these variations and modifications would fall within the scope of the present invention which shall be as defined in the claims thereof.

What is claimed is:

1. A method of preparing a sample for transmission electron microscopy (TEM), comprising:
providing a sample with two pits and a failure region between the two pits, the failure region comprising a semiconductor device;
milling a first surface of the failure region until the cross section of the semiconductor device is exposed;
etching the first surface of the failure region;
cleaning the sample; and
milling a second surface of the failure region until the failure region can be passed by an electron beam.

2. The method according to claim 1, wherein the first surface of the failure region is etched by a mixed acid solution.

3. The method according to claim 2, wherein the first surface of the failure region is etched for 7 s-9 s.

4. The method according to claim 2, wherein the mixed acid solution comprises nitrate acid, hydrofluoric acid, acetic acid, and copper sulfate.

5. The method according to claim 4, wherein the mass percentage of the nitrate acid is 45%-60%, and the mass percentage of the hydrofluoric acid is 4.5%-5%.

6. The method according to claim 5, wherein the nitrate acid is 10 ml-15 ml; the hydrofluoric acid is 5 ml-10 ml; the acetic acid is 80 ml-100 ml; and the copper sulfate is 0.2 g-0.5 g.

7. The method according to claim 1, wherein the first and second surfaces of the failure region are milled by FIB.

8. The method according to claim 1 or 7, wherein the first surface and the second surface of the failure region are milled by FIB with a current of 300 pA-500 pA.

9. The method according to claim 1, wherein the sample is cleaned by distilled water or deionized water for 60 s-120 s.

10. The method according to claim 1, wherein the second surface of the failure region is milled until the thickness of the failure region which can be passed by an electron beam is 80 nm-120 nm.

11. The method according to claim 3, wherein the mixed acid solution comprises nitrate acid, hydrofluoric acid, acetic acid, and copper sulfate.

12. The method according to claim 11, wherein the mass percentage of the nitrate acid is 45%-60%, and the mass percentage of the hydrofluoric acid is 4.5%-5%.

13. The method according to claim 12, wherein the nitrate acid is 10 ml-15 ml; the hydrofluoric acid is 5 ml-10 ml; the acetic acid is 80 ml-100 ml; and the copper sulfate is 0.2 g-0.5 g.

14. The method according to claim 7, wherein the sample is cleaned by distilled water or deionized water for 60 s-120 s.

15. The method according to claim 7, wherein the second surface of the failure region is milled until the thickness of the failure region which can be passed by an electron beam is 80 nm-120 nm.

* * * * *